United States Patent
Shahinian

(10) Patent No.: US 7,601,119 B2
(45) Date of Patent: Oct. 13, 2009

(54) REMOTE MANIPULATOR WITH EYEBALLS

(76) Inventor: Hrayr Kamig Shahinian, 8635 W. Third St., Suite 1170W, Los Angeles, CA (US) 90048

( * ) Notice: Subject to any disclaimer, the term of this patent is extended or adjusted under 35 U.S.C. 154(b) by 346 days.

(21) Appl. No.: 11/410,578

(22) Filed: Apr. 25, 2006

(65) Prior Publication Data

US 2007/0249932 A1 Oct. 25, 2007

(51) Int. Cl.
*A61B 1/05* (2006.01)
*A61B 1/005* (2006.01)
(52) U.S. Cl. .................. 600/111; 600/104; 600/144; 600/166
(58) Field of Classification Search ............ 600/111, 600/166, 104, 106, 173, 182, 144; 348/45, 348/65
See application file for complete search history.

(56) References Cited

U.S. PATENT DOCUMENTS

| | | | |
|---|---|---|---|
| 4,651,201 A * | 3/1987 | Schoolman ............ 348/45 |
| 4,759,348 A * | 7/1988 | Cawood ............ 600/102 |
| 4,951,676 A | 8/1990 | Collet-Billon |
| 5,050,226 A | 9/1991 | Collet-Billon |
| 5,536,234 A | 7/1996 | Newman |
| 5,540,229 A | 7/1996 | Collet-Billon et al. |
| 5,547,455 A | 8/1996 | McKenna et al. |
| 5,605,532 A | 2/1997 | Schermerhorn |
| 5,662,584 A | 9/1997 | Hori et al. |
| 5,667,473 A * | 9/1997 | Finn et al. ............ 600/104 |
| 5,697,891 A | 12/1997 | Hori |
| 5,751,341 A | 5/1998 | Chaleki et al. |
| 5,782,752 A | 7/1998 | Lichtman et al. |
| 5,817,014 A | 10/1998 | Hori et al. |
| 5,823,940 A | 10/1998 | Newman |
| 5,841,887 A | 11/1998 | Kuwayama et al. |
| 5,855,549 A | 1/1999 | Newman |
| 5,895,350 A | 4/1999 | Hori |
| 5,928,137 A * | 7/1999 | Green ............ 600/160 |
| 5,935,057 A | 8/1999 | Lichtman et al. |
| 5,941,817 A | 8/1999 | Crawford |
| 5,941,818 A | 8/1999 | Hori et al. |

(Continued)

FOREIGN PATENT DOCUMENTS

EP 0469966 B1 2/1992

(Continued)

OTHER PUBLICATIONS

Researchers Work on Snake-Like 'Rescue Robots', downloaded on Apr. 20, 2006 from http://www.foxnews.com/printer_friendly_story/0,3566,1924300,0.htm.

(Continued)

*Primary Examiner*—John P Leubecker
(74) *Attorney, Agent, or Firm*—Thorne & Halajian, LLP

(57) ABSTRACT

A manipulator includes a distal end having a manipulating instrument configured for manipulation at a manipulation site, and a proximate end connectable to an interface. A pair of detectors is configured to capture stereoscopic images of the manipulation site. The pair of detectors and manipulating instrument are connected to the interface, by at least a flexible guide and a wired and/or wireless communication link. The detectors are co-locatable at the manipulation site with the manipulating instrument and may be removable attached to manipulating instrument. A force detector may also be removable attached to manipulating instrument.

39 Claims, 3 Drawing Sheets

U.S. PATENT DOCUMENTS

Figure 1:
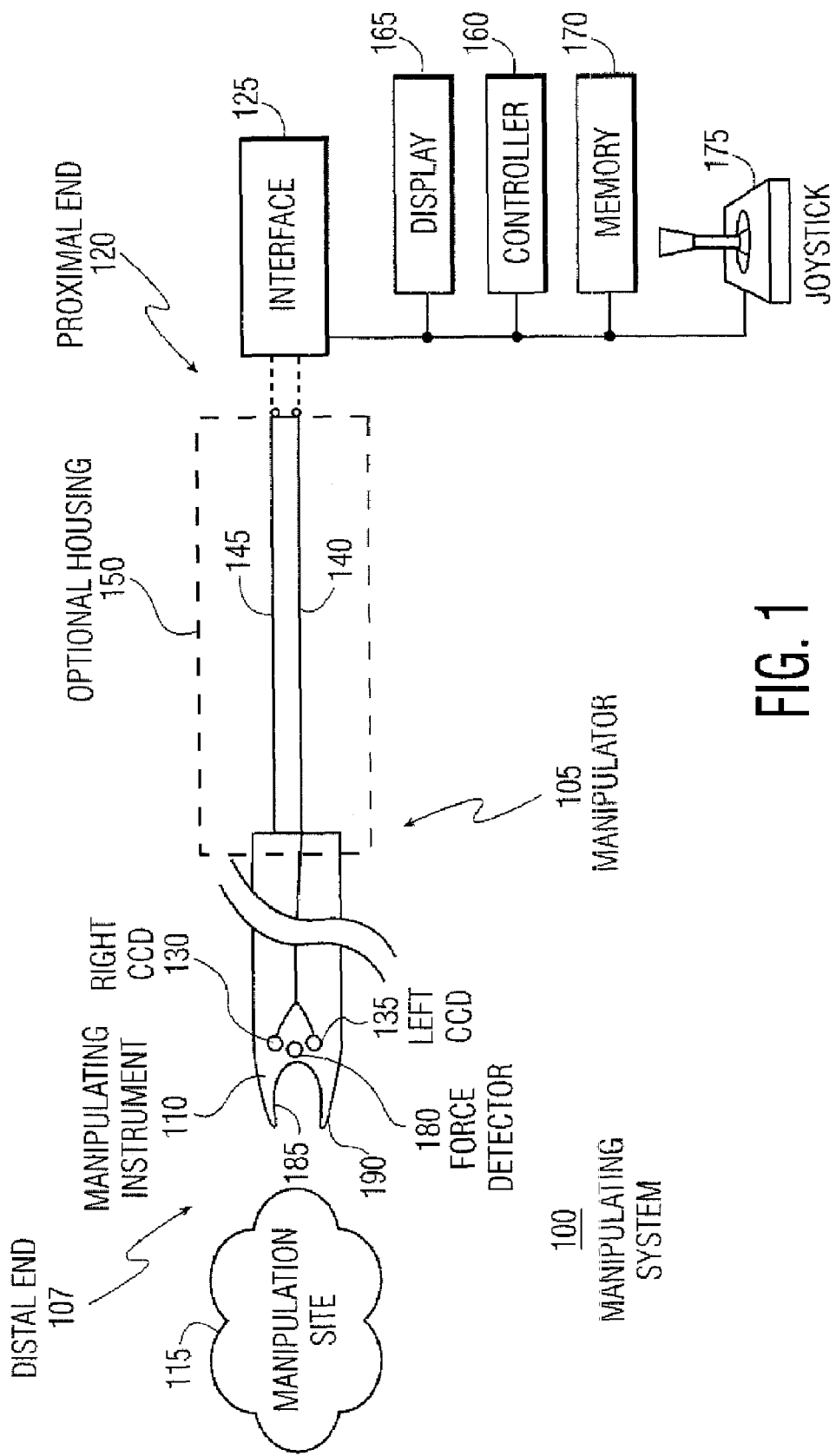

| | | | |
|---|---|---|---|
| 5,944,654 | A | 8/1999 | Crawford |
| D415,146 | S | 10/1999 | Hori |
| 5,989,182 | A | 11/1999 | Hori et al. |
| 6,046,727 | A | 4/2000 | Rosenberg et al. |
| 6,066,090 | A * | 5/2000 | Yoon ............ 600/113 |
| 6,086,528 | A * | 7/2000 | Adair ............ 600/104 |
| 6,159,146 | A * | 12/2000 | El Gazayerli ........ 600/106 |
| 6,191,809 | B1 | 2/2001 | Hori et al. |
| 6,211,848 | B1 | 4/2001 | Plesniak et al. |
| 6,223,100 | B1 | 4/2001 | Green |
| 6,277,064 | B1 * | 8/2001 | Yoon ............ 600/114 |
| RE37,356 | E | 9/2001 | Hori et al. |
| 6,290,649 | B1 | 9/2001 | Miller et al. |
| 6,292,221 | B1 | 9/2001 | Lichtman |
| 6,313,883 | B1 | 11/2001 | Thaler |
| 6,445,814 | B2 | 9/2002 | Iijima et al. |
| 6,450,948 | B1 | 9/2002 | Matsuura et al. |
| 6,647,792 | B2 | 11/2003 | Ogawa |
| 6,731,988 | B1 | 5/2004 | Green |
| 6,817,973 | B2 * | 11/2004 | Merril et al. ........ 600/118 |
| 6,832,984 | B2 * | 12/2004 | Stelzer et al. ........ 600/106 |
| 6,976,956 | B2 * | 12/2005 | Takahashi et al. ....... 600/166 |
| 6,980,676 | B2 | 12/2005 | Pineau |
| 6,991,602 | B2 * | 1/2006 | Nakazawa et al. ........ 600/101 |
| 6,997,871 | B2 * | 2/2006 | Sonnenschein et al. ..... 600/173 |
| 7,043,062 | B2 | 5/2006 | Gerard et al. |
| 2002/0030678 | A1 | 3/2002 | Ostermann |
| 2002/0049367 | A1 * | 4/2002 | Irion et al. .......... 600/173 |
| 2004/0249367 | A1 * | 12/2004 | Saadat et al. .......... 606/1 |
| 2005/0065657 | A1 | 3/2005 | Green |
| 2005/0065658 | A1 | 3/2005 | Green |
| 2005/0234296 | A1 * | 10/2005 | Saadat et al. .......... 600/129 |
| 2005/0234297 | A1 * | 10/2005 | Devierre et al. .......... 600/153 |
| 2006/0015008 | A1 * | 1/2006 | Kennedy ............ 600/109 |
| 2006/0111614 | A1 * | 5/2006 | Saadat et al. .......... 600/140 |
| 2007/0173689 | A1 * | 7/2007 | Ozaki et al. .......... 600/111 |

FOREIGN PATENT DOCUMENTS

| | | |
|---|---|---|
| FR | 2 847 995 | 6/2004 |
| JP | 04-021105 | 1/1992 |
| JP | 06-202004 | 7/1994 |
| JP | 10-010468 | 1/1998 |
| JP | 2000-052289 | 2/2000 |
| WO | WO 93/13916 A1 | 7/1993 |
| WO | WO 96/35975 A1 | 11/1996 |
| WO | WO 99/57900 A1 | 11/1999 |
| WO | WO 00/61009 A1 | 10/2000 |

OTHER PUBLICATIONS

NASA Infrared Camera Helps Surgeons Map Brain Tumers, Jul. 15, 2004, downloaded on Apr. 24, 2006 from http://www.jpl.nasa.gov/news/news.cfm?release=2004-183.

Fung et al., "A Case Study of 3D Stereoscopic vs. 2D Monoscopic Tele-Reality in . . ." IEEE/RSJ International Conference on Intelligent Robots and Systems, 2005, pp. 181-186.

Nain et al., "Three-Dimensional Nanoscale Manipulation and Manufacturing Using Proximal Probes: Controlled Pulling of Polymer . . ." IEEE Int Conf Rob Autom vol. 1, 2004, pp. 434-439.

Lytle et al., "Adapting a Teleoperated Device for Autonomous Control Using Three-Dimensional Positioning sensors: . . ." Automation in Construction, vol. 13, 2004, pp. 101-118.

Mezouar et al., "Robustness of Central Catadioptric Image-based Visual . . ." IEEE RSJ Int. Conf. Intell. Robots and Syst. IROS, vol. 2, Sep. 28-Oct. 2, 2004 Sendai, JP, pp. 1389-1394.

Murakami et al., "Automatic Insertion Work Based on Visual Measurement and Contact Force Estimation" Proc IEEE Int Conf Rob Autom, vol. 4, May 2002, pp. 4167-4172.

Trivedi et al., "A Vision System for Robotic Inspection and Manipulation", DE90 005412, Univ of Tennessee, Revised Mar. 1989, pp. 1-12.

Nguyen et al., "3D Model Control of Image Processing" In JPL, California Inst. of Tech., Proceedings of the NASA Conference on Space Telerobotics, vol. 3, pp. 213-222, May 2000.

Stiel et al. "Digital Flashing Tomosynthesis: A Promising Technique for Angiocardiographic Screening" IEEE Transactions on Medical Imaging, Jun. 1993, No. 2, NY, pp. 314-321.

* cited by examiner

REMOTE MANIPULATOR WITH EYEBALLS

The present invention relates generally to a method and system having at least one manipulator with eyeballs for providing stereoscopic vision of a remote manipulation site.

Remote manipulating, such as using robots, is becoming more prevalent, particularly for difficult to reach manipulation and/or observation sites, such as remote and/or tight spaces, or for handling potentially hazardous material including chemicals, radioactive, explosive and infectious material, etc. Even if the material being handled or manipulated is not potentially hazardous, remote manipulation is important for manipulating sites, whether or not such sites are easily accessible directly. Space exploration, medical surgery and mining operations are some examples of such manipulation and/or observation sites, which may also include other sites.

One system which is used in endoscopy or minimally invasive medicine, referred to as the Hopkins rod lens system, illuminates and thus facilitates endoscopic diagnosis and removal of foreign bodies inside a patient, where an endoscope is inserted either through natural body openings or small incisions. The interior of the body may be viewed through the scope. The Hopkins rod lens system includes a wide-angle lens at the distal end of the endoscope, and an eyepiece at the proximal end for viewing distal images. A fiberscope is provided inside the endoscope. The fiberscope has a flexible fiber optic bundle that interconnects the distal lens and the proximal eyepiece. The eyepiece may be connected to a camera. Typically, an additional fiber optic is also provided inside the endoscope for directing light from a light source outside the body, i.e., from the proximal end, to illuminate the distal end for clearer viewing. All fiberscopes introduce a certain amount of image distortion similar to the distortion of modem night vision equipment.

To enhance remote manipulation, cameras are used to provide visual images of the manipulation sites. Advances lead to the use of two cameras to provide stereoscoping images of the manipulation sites where right and left cameras provide different images to the right and left eye, simultaneously or alternately, where the different images may also be projected onto a display device or screen, for viewing through glasses or goggles worn by the manipulator.

Typically, the cameras are provided on a holding instrument or a housing which is separate from the manipulating instrument. For example, in medical applications, cameras may be provided alongside an endoscope, or on the endoscope through which (or alongside of the endoscope) a manipulating instrument is inserted. The manipulating instrument may include a laser or ultrasound source for performing minimally invasive surgery, detectors and sensors to measure internal body characteristics, or other devices, such as balloons configured to be inflated in the manipulation site, such as vessels, to provide for insertion of other instruments or to maintain the vessel diameter and prevent vessel collapsing, for example. Endoscopy equipment is produced by imaging companies such as Stryker Corporation, Fujinon, PENTAX, Olympus and Karl Storz.

Telesurgery using robotic systems allows a surgeon to operate from a site remote from the patient. The first transatlantic surgery is referred to as the Lindbergh Operation. Pill-sized endoscopic capsules have also been used with a camera, referred to as capsule cameras. For example, 1 cm×2 cm endoscopic capsules can capture 0.4 megapixel video at up to 30 frames/second. Physicians may even be provided with rotational control over the capsule to adjust the camera direction, take tissue samples and deliver medications to the patient's body.

Capsule cameras, endoscopic capsules or video pills are being promoted as alternatives to endoscopy. However capsules cannot be navigated and controlled precisely and thus cannot be used for operations requiring precision, such as brain or eye surgery and the like. Capsule cameras are primarily used to visualize the small intestine. Whereas the upper gastrointestinal tract (esophagus, stomach, and duodenum) and the colon (large intestine) can be adequately visualized with scopes having cameras placed at the proximal end of a thin flexible tube. The capsule camera can wirelessly transmit two images every second to a receiver carried by the patient. The main uses today are for detecting the cause of gastrointestinal bleeding, and for inflammatory bowel disease, such as Crohn's disease. Currently, capsule cameras do not provide stereoscopic images.

The following publications and patents provide examples of prior art devices having cameras to provide stereoscopic images, for example. All of these publications and patents are incorporated by reference as if set out in their entirety herein:

U.S. Pat. No. 5,751,341 to Chaleki, entitled "Stereoscopic Endoscope System;"

U.S. Patent Application Publication No. 2005/0065658 to Green, entitled "Flexible Robotic Surgery System and Method;"

U.S. Patent Application Publication No. 2005/0065657 to Green, entitled "Computed pivotal center surgical robotic system and method;"

U.S. Pat. No. 6,731,988 to Green, entitled "System and Method for Remote Endoscopic Surgery;"

U.S. Pat. No. 6,223,100 to Green, entitled "Apparatus and Method for Performing Computer Enhanced Surgery with Articulated Instrument;"

WO 96/35975 to White, entitled "Device and Method for Superimposing Images in a Three-Dimensional Setting without Using Lenses;"

FR 02847995 A1 to Trousset, entitled "Procede of Treatment of Information of Order Transmitted by a Peripherique of Handling of Images of Modelisation 3D, and Installation for the Visualization of Medical Images in Room of Intervention and/or Examination;"

U.S. Pat. No. 6,290,649 to Miller, entitled "Ultrasound Position Sensing Probe;"

U.S. Pat. No. 6,211,848 to Plesniak, entitled "Dynamic Holographic Video with Haptic Interaction;"

U.S. Pat. No. 6,046,727 to Rosenberg, entitled "Three Dimensional Position Sensing Interface with Force Output;"

U.S. Patent Application Publication No. 2006/0055773 to Kutka, entitled "Device and method for stereoscopic reproduction of picture information on a screen;"

U.S. Patent Application Publication Nos. 2006/0038880 and 2006/0038881 to Starkweather, entitled "Stereoscopic image display;"

U.S. Patent Application Publication No. 2006/0036383 to Clare, entitled "Method and device for obtaining a stereoscopic signal;"

U.S. Patent Application Publication No. 2006/0012753 to Gandara, entitled "Stereoscopic imaging;"

U.S. Patent Application Publication No. 2006/0012674 to Kao, entitled "Image display system and method;"

U.S. Patent Application Publication No. 2006/0082644 to Tsubaki, entitled "Image processing apparatus and image processing program for multi-viewpoint image;" and U.S. Patent Application Publication No. 2006/0080878 to Kittrell, entitled "Three-dimensional display frame assembly."

There is a need to provide for smaller manipulator systems having three-dimensional (3-D) and/or stereoscopic vision that can be precisely controlled for accurate manipulation and visualization of a manipulation site being manipulated with a manipulator of the manipulator systems.

According to one embodiment of the system, a manipulator includes a distal end having a manipulating instrument configured for being manipulated at a manipulation site, and a proximate end connectable to an interface. A pair of detectors at the distal end is configured to capture stereoscopic images of the manipulation site. The pair of detectors and manipulating instrument are connected to the interface, by at least a flexible guide and a wired and/or wireless communication link. The detectors are co-locatable at the manipulation site with the manipulating instrument and may be removable attached to the manipulating instrument. A force detector may also be removably attached to manipulating instrument. Of course, in addition to, or instead of, being connected to the interface, the proximate end may simply be configured for manual manipulation by the operator, for example, to guide the manipulating instrument and perform desired operations by hand. The manipulating instrument, the pair of detectors, one detector, and/or multiple detectors may be attached to the flexible guide. Upon guidance to the desired position, the flexible guide may be rendered rigid to hold the manipulating instrument and/or detector(s) in the desired position.

According to another embodiment, a method of remotely manipulating a manipulation site includes the acts of:

providing a manipulating instrument at the manipulation site;

providing a pair of detectors on the manipulating instrument, the pair of detectors being removably attached to the manipulating instrument; and controlling the pair of detectors to capture stereoscopic images of the manipulation site.

These and other features, aspects, and advantages of the apparatus and methods of the present invention will become better understood with regard to the following description, appended claims, and accompanying drawings where:

FIG. 1 shows an illustrative embodiment of a remote manipulator system according to the present system; and FIGS. 2-5 show various embodiment of manipulator instruments and detectors of the remote manipulator system according to the present system.

The present system will be explained below in the context of an illustrative implementation related to medical applications. However, it is to be understood that the present invention is not limited to a particular application or structural embodiment. Rather, the invention is more generally applicable to any manipulator for manipulating any remote manipulation site related to any suitable application such as space exploration, medical surgery, mining operations, inspection of equipment, where it is desirable to improve remote manipulation, examination and vision of manipulation sites, such as sites with small tightly packed components (in an equipment, a biological body, or otherwise) that are not easily accessible. Other applications and uses of the manipulator include machining, computer repair, clandestine monitoring, locksmithing, safecracking, and computer forensics, rescue operations in collapsed structures, etc.

Referring now to FIG. 1, there is shown an illustrative embodiment of a manipulator system 100 having a manipulator 105. The manipulator 105 includes an interface device 125 at its proximal end 120, as wells as a manipulating instrument 110 and a pair of detectors 130, 135 at its distal end 107. The interface device 125, the manipulating instrument 110 and the pair of detectors 130, 135, as well as other elements of the manipulator system 100, individually or collectively may be part of, or integrated with, the manipulator 105, or may be fixedly or removably attachable to the manipulator 105 or to further flexible guides. For example, the detectors 130, 135 may be integrated with a controllable moving mechanism to form a detection system that may be clipped, snapped, screwed or otherwise removably attached to the manipulating instrument 110, or to its own flexible guide, e.g., via Velcro type of mechanism, small magnets having low magnetic fields that do not provide noticeable interference or the like.

The controllable moving mechanism may provide pan/tilt/zoom function for moving the detectors 130, 135 in unison for 3-D imaging, or moving each detector independently for 2-D imaging if needed, such as in tights spaces or around corners with room for only one of the detectors.

The manipulating instrument 110 may be any kind of instrument configured to manipulate or monitor any suitable manipulation site 115. Illustratively, the manipulating instrument 110 is a medical instrument used in minimally invasive surgery, where it is inserted into a patient through a small incision site or natural body opening, and is directed to a desired location or manipulation site 115 for performing a medical operation, be it mere probing and taking measurements of bodily functions or removal of unwanted tissue, such as through cutting, heating, cooling or pulverizing through any suitable means such as using razors, lasers, ultrasound or cryogenic devices. Of course, the manipulating instrument 110 and manipulation site 115 need not be related to medicine. By way of non-limiting examples, manipulating instruments and sites may be related to handling or monitoring material and sites that are potentially hazardous including chemicals, radioactive, explosive and infectious material and sites, etc. Further, the manipulating instrument 110 may be used remotely in remote sites, such as related to space and underwater explorations, mining operations, remote medical operations, rescue operations, etc.

The pair of detectors 130, 135 is separated by a predetermined known distance, which may be variably controlled so as to provide three-dimensional (3-D) stereoscopic images with depth perception as is well known in the art of 3-D imaging, where knowing the separation distance between the two detectors, which may be charge-coupled device (CCD) cameras, right and left images (which are different from each other) are alternately or simultaneously provided on a display monitor or directly in the retina/eye of the operator. Of course, various mirrors, objective lens types or systems may be also be provided, e.g. in front of the CCDs 130, 135, such as for providing wide angle, panoramic and/or zoom views. Further multiple detectors may also be provided that are configured to capture and create holographic images of the manipulation site which are projected for viewing by multiple users, in addition to the operator of the manipulator 105. U.S. Pat. No. 5,751,341 to Chaleki, entitled "Stereoscopic Endoscope System" describes two CCDs configured to provide 3-D stereoscopic images, with associated objective lens systems, controllers or processors, sensors, display monitors, projectors and special polarized eyeglasses or passive and active eyewear or headsets for 3-D viewing, communication means, movement/rotation/guidance means and the like. As is also well know in the art, the distance between the eyes of the viewer/operator may also be taken into account for improved 3-D viewing, as described in U.S. Patent Application Publication Nos. 2006/0055773, 2006/0038880, 2006/0038881, 2006/0036383, 2006/0012753, and 2006/0012674. Heads up displays for providing 3-D and/or stereoscoping images of the manipulation site may also be provided.

It is desirable to have a set default separation (which may be programmable and thus also controllable to provide better images, e.g., to suit the distance between the operator's eyes)

between the pair of detectors 130, 135 so that the detectors return to the default position (e.g., after being independently controlled and moved), such as in response to a user input (such as an activation of a button on the interface 125 and/or joystick 175), or automatically in response to detection of unacceptable rendered images. The rendered images, such as displayed or projected on a medium, (whether 2-D or 3-D, such as stereoscopic or holographic images,) or directly into the viewer's eyes, include images of the manipulation site 115, captured by the pair of detectors 130, 135 and/or further multiple detectors, which may be provided as needed for capturing holographic images.

In the case of stereoscopic images, the right detector 130 captures a right image of the manipulation site 115, and the left detector 135 captures a left image which is different from the right image. The right and left images are then simultaneously or alternately provided to a medium, e.g., a screen, a liquid crystal display (LCD) or plasma monitor, or directly to the right and left eyes of a user of the manipulator system 100. High definition (HD) images may be displayed on small right and left HD LCD or plasma displays mounted on eyewear or headset worn by the user, for providing different right and left images in front of or to the right and left user eyes, resulting in a 3-D image as viewed by the user. Of course, other gear may also be used for viewing the 3-D stereoscopic or holographic images, such as helmets configured to provide heads-up displays on suitable mediums or surface(s) as described. It should be noted that reference to 3-D images is not limited to stereoscopic images, and may also include other images, such as holographic images. Similarly, reference to stereoscopic images may include other type of 3-D images such as holographic images.

Illustratively, the right and left images are simultaneously or alternately displayed or projected on the medium so as to provide 3-D stereoscopic images with depth perception. As is well know in the art of 3-D imaging, there are various ways to provide 3-D imaging for viewing with or without special glasses having special lenses such as lenses with different polarization, as described in U.S. Patent Application Publication No. 2005/0065658 to Green, entitled "Flexible Robotic Surgery System and Method;" U.S. Patent Application Publication No. 2005/0065657 to Green, entitled "Computed pivotal center surgical robotic system and method;" U.S. Pat. No. 6,731,988 to Green, entitled "System and Method for Remote Endoscopic Surgery;" U.S. Pat. No. 6,223,100 to Green, entitled "Apparatus and Method for Performing Computer Enhanced Surgery with Articulated Instrument." Some of the other well known methods of forming and viewing 3-D images include using parallax computed holographic displays, as described in U.S. Pat. No. 6,211,848 to Plesniak, entitled "Dynamic Holographic Video with Haptic Interaction."

As is well known in the art of 3-D imaging, it may be desirable to configure the 3-D images for viewing without any special glasses, as described in WO 96/35975 to White, entitled "Device and Method for Superimposing Images in a Three-Dimensional Setting without Using Lenses." For example, the right and left images may be simultaneously or alternately projected directly into the operator's eyes, or onto lenses of glasses worn by the user of the manipulator system 100. Of course, the images may also be projected on any desired projection surface such as a heads-up displays where, for example, the user wears a helmet, goggles, glasses or any other headpiece, where right and left images are projected onto the right and left lenses of the headpiece, or onto small right and left HD LCD or plasma displays located a few inches away form the user's eyes. Of course, the images of the manipulation site 115 may also be provided as holographic images projected onto a medium for viewing by multiple viewers.

Typically, for precision operations such as medical procedures, as well as operations dealing with hazardous material including explosive, chemical, biological, radioactive material and the like, or operations in limited space such as mining operation including space and underwater exploration, it is desirable to have a footprint, e.g., diameter, of the manipulator 105 that substantially matches the manipulation site, or at least an access opening thereof. In an illustrative example related to medical surgical operations, it is desirable to have the manipulator footprint be as small as possible, particularly for minimumally invasive operations, where the manipulator 105 is inserted into the body through a small incision of less than 10 mm, typically of the order of 2-4 mm, where each CCD is approximately 1-2 mm or less, and is located substantially at the tip of the manipulating instrument 110, including being rotateable and movable in any direction or orientation, e.g., controlled by the interface 125 or a control device, such as a joystick 175, or manually controllable by the operator hand(s), to provide eyeballs on the manipulating instrument 110 capable of providing images around corners or obstacles etc.

Currently, endoscopes are used having a housing through which various instruments are inserted into the body where CCD cameras may be provided on the endoscope housing, as described in U.S. Pat. No. 5,751,341. The present system dispenses with the housing to further reduce the instrument footprint as well as reduce the size of the incision or required entry/access opening. The reduced footprint allows insertions and guidance of the manipulating system 100 through reduced openings, and provides for better and more precise guidance and manipulation of the manipulator 105 to the manipulation site 115.

The detectors 130, 135 are connectable to the interface 125 through a first connection 140, while the manipulating instrument 110 is connectable to the interface 125 through a second connection 145. Of course, the two connections may be integrated into a single connection that provides for electrical and/or mechanical connection of the detectors 130, 135 and manipulating instrument 110 with the interface 125. The electrical connections may be a wired or wireless connections for communication amongst the various system elements, such as amongst the detectors 130, 135, manipulating instrument 110, interface 125, controller/processor 160, memory 170, force detector 180, display 165 and a control interface, such as the joystick 175, roller ball and the like. The wired connection may by any means such as using conductors or fiber optics. Similarly, any type of wireless communications may be used, such as Bluetooth for example, in the case of the various elements are in relatively close proximity to each other. Of course, signals for communication and control for example may also be communicated via other networks, whether local area networks (LANs) or wide area networks (WANs), such as the Internet. Signals may also be communicated over very long ranges, such as the case for space exploration.

The mechanical connection between one or both detectors 130, 135 and/or the manipulating instrument 110 on one hand, and the interface 125 and/or a holder for manual manipulation (by the operator to manipulate the holder) on the other hand may be through a guide(s) which may also provide an electrical/optical communication link in addition to a mechanical link. The guide(s) 140, 145 may be flexible in one state for advancing and guiding the detectors 130, 135 and/or manipulating instrument 110 to the manipulation site 115. Once the detectors 130, 135 and/or manipulating instrument 110 are positioned in the desired location, the flexible guide(s) may be rendered rigid to hold the detectors 130, 135 and/or manipulating instrument 110 in the desired position(s), or to allow for more precise manipulation and control. For example, the guide(s) may be formed from a material that changes state in response to a stimuli, such as an electric current, and electromagnetic field, as well as in response to changes in pneumatic or hydraulic pressure, which may be provided in response to operator action for example, where fluid such as air or liquids may be forced into a hollow flexible guide (or a guide having a channel), where a certain pressure is maintained, thus rendering the guide as rigid as desired. The flexibility and malleability of the guides may also be changed in response to detecting a predetermined force, for example, to prevent damage to the environment or manipulation site by pushing or pulling the guides too hard in their rigid state. When a manipulating force exerted on the detectors 130, 135 and/or manipulating instrument 110 exceeds the predetermined threshold, which may be automatically or manually variably set in response to detecting the softness or hardness of the environment, the state of the guides may change from rigid to flexible, for example. The degree of flexibility and/or rigidity may also be controllable to achieve, manually or automatically, the desired amount or degree of flexibility/ rigidity.

The rigid state of the guide(s) holding the detectors 130, 135 may include a predetermined position or separation between to the two or more detectors 130, 135 for providing suitable 3-D stereoscopic and/or holographic images. Thus, in response to user activation or detection of unacceptable images, the separation between the two detectors 130, 135 returns to a predetermined programmable value.

As shown in FIG. 1, the controller 160 is connectable to the interface 125, and is configured to control movement of the manipulating instrument 110 and the pair of detectors 130, 135. As already described, an operator such as a surgeon may hold the proximal end, e.g., via a suitable holder or interface 125, to manually control the manipulating instrument 110 and/or the detectors 130, 135. Accordingly, it should be understood that the interface 125 includes the hand of the operator, a robotic arm controlled by the operator via the joystick 175 for example, and/or any other suitable device configured to provide manipulation of the manipulating instrument 110 and/or the detectors 130, 135. A display device 165 is also connectable to the interface 125, where the controller 160, alone or in conjunction with a display controller of the display device 165, processes stereoscopic images received from the pair of detectors 130, 135 for display on the display device 165.

The manipulating instrument 110 and/or the pair of detectors 130, 135 may be connected to the interface 125 by a flexible shaft(s) or guide(s) that includes the connections 140, 145, e.g., having a guide(s) with different states (rigid and flexible) as described, for insertion and guidance thereof to the manipulation site 110. Illustratively, one guide is provided between the manipulating instrument 110 and the interface 125, where the pair of detectors 130, 135 is mounted on the manipulation site 110, and may also communicate with the interface 125 through the guide which may include the connections 140, 145, such as wire, fiber optic, etc. Alternatively, or in addition, the pair of detectors 130, 135 communicates with the interface 125 or directly with the controller 160 and/or the display 165 by other means, such as by wireless communication, where wireless communication may also be used in addition to, or instead of, wired communication between the manipulating instrument 110 and the controller 160 and/or other devices, such a remote controller or joystick 175.

Communication wiring and/or a fiber optic bundle itself may be used as the flexible guide thus further reducing the footprint of the manipulator 105 and the size requirement of any openings for insertion and guidance of the manipulator 105. Thus, unlike conventional endoscopes having a housing that are used for insertions of desired instruments thereto for reaching a manipulation site, the manipulation 105 does not require such a housing. Rather, the flexible guide itself is fixedly or removably attached to the manipulating instrument 110 (and/or detectors 130, 135 in the case where the detectors 130, 135 are not attached to the manipulating instrument 110 and have their own flexible guide(s)) for insertion and guidance thereof to the manipulation site 115.

Of course, an optional housing 150 may be provided if desired. In this case, the housing 150 itself need not reach or be inserted all the way to the manipulation site. Rather, the pair of detectors 130, 135, which are not mounted on the housing, but rather are mounted on the manipulation instrument 110 itself (or provided on separate a flexible guide(s) that may be rendered rigid as described), may extend beyond the housing 150 to reach or be closer to the manipulation site 115 than the housing 150, and/or be co-located at the manipulation site 115 with the manipulating instrument 110.

Figure 2:
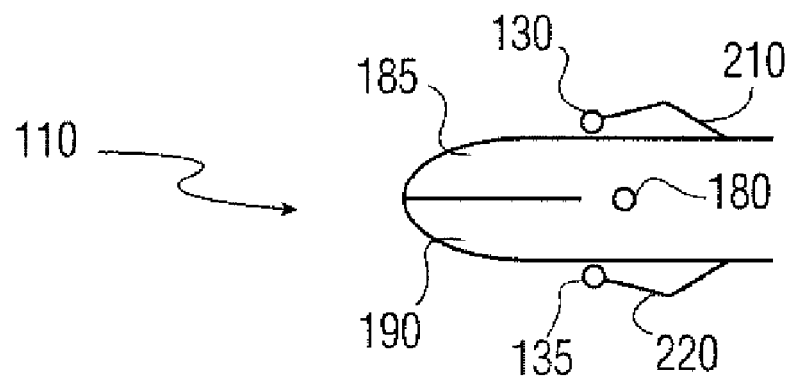
Figure 3:
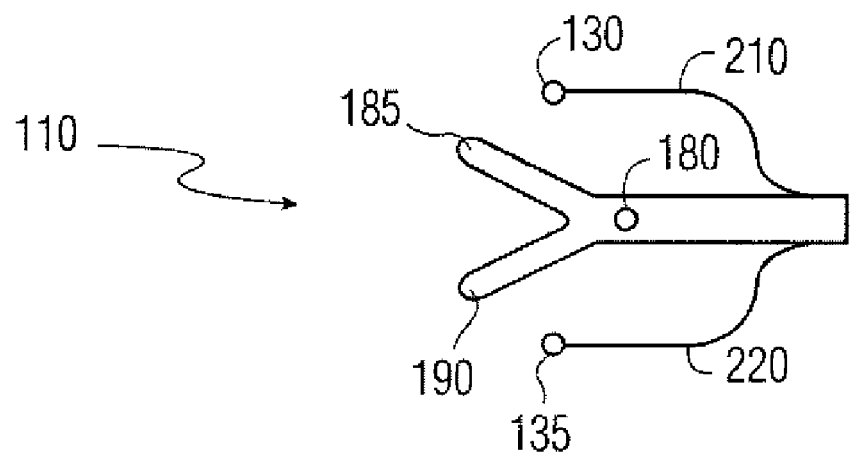

FIG. 2-3 show another embodiment of the manipulator instrument 110 and detectors 130, 135 in greater detail. As shown in FIGS. 2-3, the detectors 130, 135 are attachable to the manipulator instrument 110 and each may have its own attachment member 210, 220 which may be telescopic and thus extendable under the control of the controller 160. The attachment members 210, 220 and thus the detectors 130, 135 may be fixedly attached at a fixed distance therebetween. Alternatively, the detector member 210, 220 may be movable in unison to change direction and orientation of the detectors 130, 135. It should be noted that the distance between the two detectors 130, 135 may be maintained at a fixed distance while their direction and orientation are changed in unison. Alternatively, the distance between the two detectors 130, 135 may be changed by moving apart or closer the detector members 210, 220, as shown in FIG. 3. Each detector may be independently moveable, for example, to provide mono-images of desired areas where stereoscopic images may be difficult to obtain, such as when both detectors cannot be moved in unison to point to a particular direction.

The distance between the two detectors 130, 135 may be continuously changeable or changed between predetermined values. For examples, the separation or distance between the two detectors 130, 135 may be selectable from a set of predetermined values, such as 1 mm, 1.2 mm, 1.4 mm etc. Alternatively or additionally, the distance may be stepped in programmable steps or increments, or directly changed from one value to another, such as from 1 mm to 2 mm. As is well known in the art, the distance between the two detectors 130, 135 is used by a processor or controller to generate the 3-D images. The distance between the two detectors 130, 135 may be determined in view of their moving apart or together in known predetermined or programmable steps. Alternatively or in addition, sensors may be provided to measure and calculate the distance between the two detectors 130, 135.

Figure 4:
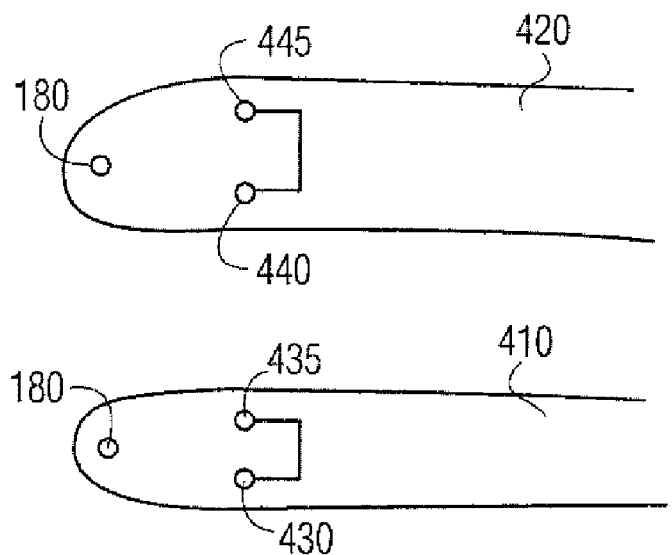

The detectors 130, 135 themselves, their members 130, 135, or the detector(s)-member(s) combination(s) may each be removably attachable to the manipulator instrument 110. Of course, in the case where more than one manipulator instrument 110 is provided, each or any desired number of manipulator instruments may have their own pair of detectors to provide 3-D stereoscopic images of the site where the particular manipulator instrument is pointed to. For example as shown in FIG. 4, one manipulator instrument 410 may be configured to cut or pulverize a tumor, while another manipulator instrument may be configured for suction of the cut/pulverized tissue. In this embodiment, each manipulator instrument 410, 420 has its own pair of detectors 430, 435 and 440, 445, respectively. Of course, any one of the manipulator instruments may only have a single detector 510, 520, as shown in FIG. 5, alone or combined with further manipulator instrument(s) 530 with pair of detectors 540, 545.

In the case where two different further manipulator instruments, each having a single detector, are moved in unison, the two detectors of each instrument may form a pair of detectors for providing 3-D stereoscopic images.

Returning to FIGS. 1-3, illustratively, the detector members 210, 220 separately or collectively are movable to orient the detector(s) to any desired direction, under the control of the controller 160, which may be manually controlled by the user of the manipulating system in a manual mode, or automatically in an automatic mode. In the automatic mode, the detectors may be configured to pan the overall region or manipulation site 115 and detect regions of anomalies which are different from neighboring areas, e.g., to map the overall area and distinguish and/or identify such areas of anomalies. Further operation and/or display modes also include stereoscopic and mono modes, where in the stereoscopic mode the two detectors 130, 135 move together separated by a known distance used for providing 3-D/stereoscopic images. In the mono mode, each detector is controlled and moved independently of each other to provide a mono-image of a site that may be located in an area where an acceptable 3-D image is difficult to obtain. For example, the right detector 130 may be independently moved (e.g., including pan/tilt/zoom) to the extreme right and even backward to provide mono views are such areas.

Figure 5:
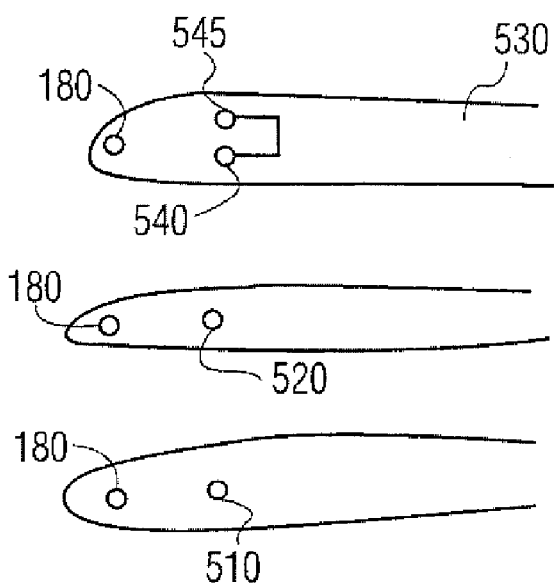

The manipulating instrument 110 may be any desired instrument suitable for a particular manipulation and may have one or more probes, where illustratively two and three probes are shown in FIGS. 4-5, respectively. The probe(s) may be configured to perform various tasks, such as pick and place, cut, heat, cool, pulverize, etc. For example in a medical application, one probe may include a laser for heating, burning, cutting tumors or shaving the capsule of a tumor or an ultrasound transducer for pulverizing unwanted tissue, while the other probe may be may configured to provide suction or the detached unwanted tissue. The probes may also be configured to collect samples, such as sample tissues for biopsy, or other samples in space, mining or underwater explorations.

Of course, the detectors 130, 135 themselves, or other detectors may be fixedly or removably attached to the probes themselves, as desired, and may include any type of detector, and are not limited to image detectors form providing images. For example, the detectors may be configured to detect hazardous or any other material, such as explosive, chemical, biological to radioactive material, as well as particular material for example associated with mining operations, such as detecting gold, diamond, coal, oil, etc., including being configured to perform tests or collect data to identify material near the manipulation site, typically used in exploration of unknown and remote areas of any object, such as a biological body, areas of earth, other planets, moons, atmosphere, space, etc.

Alternately or in addition to the image detectors 130, 135, a further detector(s) 180 may be provided configured to detect and provide force information, to allow for a refined manipulation where forces and position of the manipulating instrument relative to its environment are detected. For example, a sonar sensor(s) may be used to determine proximity or distance of objects from the sensor(s). Each manipulating instrument 110 may have its own force detector 180 or other detectors such as a sonar transceiver that transmits signals, such as sound waves to determine distance(s) to objects based on received sound waves reflected from objects. Of course, more than one sonar and/or force detector 180 may be provided on each manipulating instrument 110 as needed, such as when the manipulating instrument 110 has several members, where two such members 185, 190 are shown in FIG. 1. Thus, a force detector 180 may be provided on each member 185, 190.

The detected force is feedback to the user, in response to which actuators or force generators operate to provide a more realistic feeling of the remote manipulation site for more precise exertion of desired forces. Thus, the user feels as if being present at the remote manipulation site 110, by viewing 3-D stereoscopic images as well as feeling and interacting with the manipulation site 110 and/or a synthetic image/object thereof that simulate the properties of the manipulation site 110.

Force detectors and generators, position sensors and actuators for providing force sensation and feeling of remote sites are well known, as described in U.S. Patent Application Publication No. 2005/0065658 to Green, FR 02847995 A1 to Trousset, U.S. Pat. No. 6,290,649 to Miller, U.S. Pat. No. 6,211,848 to Plesniak, and U.S. Pat. No. 6,046,727 to Rosenberg.

The controller 160 may be any type of controller and/or processor and may be programmable, where programs, software and other data are stored in the memory 170 or additional memories that are operationally coupled to each other and the controller 160 and other elements of the manipulating system 100. Thus, the controller 160, the memory 170, the interface 125, the display 165, the joystick 175 and any other input/output (I/O) or peripheral device, may all be operationally coupled to each other as needed. The memory 170 may be any type of device for storing application data as well as other data. The various component of the system may be operationally coupled to each other by any type of link, including wired or wireless link(s), for example.

Such software can of course be embodied in any computer-readable medium, such as an integrated chip, a peripheral device or memory, such as the memory 170 or other memory coupled to the controller/processor 160, which may be a dedicated processor for performing in accordance with the present system, or may be a general-purpose processor wherein only one of many functions operates for performing in accordance with the present system. The processor may operate utilizing a program portion, multiple program segments, or may be a hardware device utilizing a dedicated or multi-purpose integrated circuit. Each of the above systems utilized for identifying the presence and identity of the user may be utilized in conjunction with further systems.

The computer-readable medium and/or memory 170 may be long-term, short-term, or a combination of long-term and short-term memories, or any recordable medium, (e.g., RAM, ROM, removable memory, CD-ROM, hard drives, DVD, floppy disks or memory cards) or may be a transmission medium (e.g., a network comprising fiber-optics, the world-wide web, cables, and/or a wireless channel using, for example, time-division multiple access, code-division multiple access, or other wireless communication systems). Any medium known or developed that can store information suitable for use with a computer system may be used as the computer-readable medium and/or memory 170.

These memories configure the processor 160 to implement the methods, operational acts, and functions disclosed herein. The memories may be distributed or local and the processor 160, where additional processors may be provided, may be distributed or singular. The memories may be implemented as electrical, magnetic or optical memory, or any combination of these or other types of storage devices. Moreover, the term "memory" should be construed broadly enough to encompass any information able to be read from or written to an address in the addressable space accessed by a processor. With this definition, information on a network is still within memory 170, for instance, because the processor 160 may retrieve the information from the network.

The processor 160 and memory 170 may be any type of processor/controller and memory, such as those described in U.S. 2003/0057887, which is incorporated herein by reference in its entirety. The processor 160 is capable of providing control signals and/or performing operations in response to input signals from the I/O devices such as the joystick 175 and/or other devices including independent control of CCD cameras 130, 135 and the manipulating instrument 110, and executing instructions stored in the memory 170. The processor 160 may be an application-specific or general-use integrated circuit(s). Further, the processor 160 may be a dedicated processor for performing in accordance with the present system or may be a general-purpose processor wherein only one of many functions operates for performing in accordance with the present system. The processor may operate utilizing a program portion, multiple program segments, or may be a hardware device utilizing a dedicated or multi-purpose integrated circuit. Each of the above systems utilized for identifying the presence and identity of the user may be utilized in conjunction with further systems.

Of course, it is to be appreciated that any one of the above embodiments or processes may be combined with one or with one or more other embodiments or processes to provide even further improvements in providing for accurate 3-D images and feeling of remote manipulation sites.

Finally, the above-discussion is intended to be merely illustrative of the present system and should not be construed as limiting the appended claims to any particular embodiment or group of embodiments. Thus, while the present system has been described in particular detail with reference to specific exemplary embodiments thereof, it should also be appreciated that numerous modifications and alternative embodiments may be devised by those having ordinary skill in the art without departing from the broader and intended spirit and scope of the present system as set forth in the claims that follow. The specification and drawings are accordingly to be regarded in an illustrative manner and are not intended to limit the scope of the appended claims.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function;

e) any of the disclosed elements may be comprised of hardware portions (e.g., including discrete and integrated electronic circuitry), software portions (e.g., computer programming), and any combination thereof;

f) hardware portions may be comprised of one or both of analog and digital portions;

g) any of the disclosed devices or portions thereof may be combined together or separated into further portions unless specifically stated otherwise; and h) no specific sequence of acts or steps is intended to be required unless specifically indicated.

What is claimed is:

1. A manipulator comprising:
   a distal end having a manipulating instrument configured for manipulation at a manipulation site;
   a proximate end connectable to an interface;
   detectors configured to capture stereoscopic images of said manipulation site; said
   detectors being configured for a first connection to said interface, and said manipulating instrument being further configured for a second connection to said interface; and
   a force detector for detecting a force at said distal end;
   wherein said detectors are co-locatable at said manipulation site with said manipulating instrument;
   wherein at least one of said first connection and said second connection includes at least one guide having a flexible state and a rigid state; and
   wherein said interface is configured to change flexibility of the at least one guide in response to said force.

2. The manipulator of claim 1, wherein said detectors are removably attachable to said manipulating instrument.

3. The manipulator of claim 1, wherein said at least one guide is configured for being in said flexible state for advancing at least one of said detectors and said manipulating instrument toward said manipulation site, and wherein said at least one guide is configured for being in said rigid state for substantially holding said at least one of said detectors and said manipulating instrument in a desired position.

4. The manipulator of claim 1, further comprising a housing configured to facilitate providing said manipulating instrument and said detectors to said manipulation site; said manipulating instrument and said detectors being extendable beyond said housing for reaching said manipulation site.

5. The manipulator of claim 1, further comprising a controller connectable to said interface; said controller being configured to control movement of at least one of said manipulating instrument and said detectors.

6. The manipulator of claim 1, further comprising a controller connectable to said interface; said controller being configured to process said stereoscopic images for display on a display device.

7. The manipulator of claim 6, wherein said display device includes at least one of a monitor, a heads-up display, a projector and eyeglasses.

8. The manipulator of claim 6, wherein said controller is configured to respond to commands from at least one of movement of a joystick and speech.

9. The manipulator of claim 1, wherein said interface is configured to allow manual manipulation of at least one of said manipulating instrument and said detectors by a user of said manipulator.

10. The manipulator of claim 1, further comprising additional detectors configured to capture three dimensional images of said manipulating instrument.

11. The manipulator of claim 10, wherein said three dimensional images are renderable as holographic images.

12. The manipulator of claim 1, wherein said force detector is removably attached to at least one of said detectors and said manipulating instrument.

13. The manipulator of claim 1, wherein said detectors are configured to move independently of each other to provide non-stereoscopic images and are configured to automatically return to a default predetermined distance between said detectors based on the rendered images.

14. The manipulator of claim 1, further comprising sensors configured to measure and calculate a distance between the detectors.

15. The manipulator of claim 1, wherein said interface is configured to change the flexibility when said force exceeds a predetermined threshold.

16. A manipulator comprising:
a distal end having a manipulating instrument configured for manipulation at a manipulation site;
a proximate end connectable to an interface;
a first detector configured to capture images of said manipulation site; said first detector being configured for a first connection to said interface, and said manipulating instrument being configured for a second connection to said interface;
a second detector located at a predetermined distance from said first detector for providing a stereoscopic image of said manipulation site; and
a force detector for detecting a force at said distal end;
wherein said first detector and said second detector are co-locatable at said manipulation site with said manipulating instrument;
wherein at least one of said first connection and said second connection includes at least one guide having a flexible state and a rigid state; and
wherein said interface is configured to change flexibility of the at least one guide in response to said force.

17. The manipulator of claim 16, wherein said first detector is removably attachable to said manipulating instrument.

18. The manipulator of claim 16, wherein said at least one guide is configured for being in said flexible state for advancing at least one of said first detector and said manipulating instrument toward said manipulation site, and wherein said at least one guide is configured for being in said rigid state for substantially holding said at least one of said first detector and said manipulating instrument in a desired position.

19. The manipulator of claim 16, further comprising additional detectors configured to capture three dimensional images of said manipulating instrument.

20. The manipulator of claim 19, wherein said three dimensional images are renderable as holographic images.

21. The manipulator of claim 16, further comprising a housing configured to facilitate providing said manipulating instrument and said first detector to said manipulation site; said manipulating instrument and said first detector being extendable beyond said housing for reaching said manipulation site.

22. The manipulator of claim 16, further comprising a controller connectable to said interface; said controller being configured to control movement of at least one of said manipulating instrument and said first detector.

23. The manipulator of claim 16, wherein said interface is configured to allow manual manipulation of at least one of said manipulating instrument and said first detector by a user of said manipulator.

24. The manipulator of claim 16, further comprising a controller connectable to said interface; said controller being configured to process said images for display on a display device.

25. The manipulator of claim 24, wherein said display device includes at least one of a monitor, a heads-up display, a projector and eyeglasses.

26. The manipulator of claim 24, wherein said controller is configured to respond to commands from at least one of movement of a joystick and speech.

27. The manipulator of claim 16, wherein said force detector is removably attached to at least one of said first detector and said manipulating instrument.

28. The manipulator of claim 16, wherein said detectors are configured to move independently of each other to provide non-stereoscopic images and are configured to automatically return to a default predetermined distance between said first detector and said second detector based on the rendered images.

29. The manipulator of claim 16, wherein said interface is configured to change the flexibility when said force exceeds a predetermined threshold.

30. A manipulation system comprising:
a manipulator having an interface at a proximal end, and a manipulating instrument and detectors at a distal end, said manipulating instrument being configured for manipulation at a manipulation site, and said detectors being separated by a predetermined distance to capture stereoscopic images of said manipulation site;
a controller connectable to said interface, said controller being configured to control movement of at least one of said manipulating instrument and said detectors;
a display device, wherein said controller is further configured to process said stereoscopic images for display on said display device; and
a force detector for detecting a force at said distal end;
wherein said detectors are extendable beyond a housing of said manipulator;
wherein at least one of said detectors is included on at least one guide having a flexible state and a rigid state; and
wherein said interface is configured to change flexibility of the at least one guide in response to said force.

31. The manipulation system of claim 30, wherein said force detector is removably attached to at least one of said detectors and said manipulating instrument.

32. The manipulation system of claim 30, wherein said detectors are configured to move independently of each other to provide non-stereoscopic images and are configured to automatically return to a default predetermined distance between said detectors based on the rendered images.

33. The manipulation system of claim 30, further comprising sensors configured to measure and calculate a distance between the detectors.

34. The manipulation system of claim 30, wherein said interface is configured to change the flexibility when said force exceeds a predetermined threshold.

35. A method of remotely manipulating a manipulation site comprising the acts of:
providing a manipulating instrument at said manipulation site;
attaching detectors to at least one guide having a flexible state and a rigid state;
controlling said detectors to move and capture stereoscopic images of said manipulation site;
detecting a force with a force detector at a distal end of said manipulating instrument; and
increasing flexibility of the at least one guide in response to said force.

36. The method of claim 35, wherein said detectors are removably attached to said manipulating instrument.

37. The method of claim 35, wherein the controlling act automatically returns said detectors to a default predetermined distance between said detectors based on the rendered images.

38. The method of claim 34, wherein the increasing act increases the flexibility when said force exceeds a predetermined threshold.

39. The method of claim 34, wherein said force detector is removably attached to said manipulating instrument.

* * * * *